US012685811B2

(12) United States Patent
Fireman

(10) Patent No.: US 12,685,811 B2
(45) Date of Patent: Jul. 21, 2026

(54) HOLDER TO SECURE AN AUTO-INJECTION DEVICE

(71) Applicant: Marnie P. Fireman, North Bethesda, MD (US)

(72) Inventor: Marnie P. Fireman, North Bethesda, MD (US)

( * ) Notice: Subject to any disclaimer, the term of this patent is extended or adjusted under 35 U.S.C. 154(b) by 539 days.

(21) Appl. No.: 17/070,092

(22) Filed: Oct. 14, 2020

(65) Prior Publication Data

US 2022/0111139 A1     Apr. 14, 2022

(51) Int. Cl.
*A45C 11/00* (2006.01)
*A61M 5/00* (2006.01)
*H04M 1/02* (2006.01)

(52) U.S. Cl.
CPC .......... *A61M 5/002* (2013.01); *H04M 1/0202* (2013.01); *A61M 2205/0216* (2013.01); *A61M 2205/0288* (2013.01); *A61M 2205/3592* (2013.01); *A61M 2205/3606* (2013.01); *A61M 2205/362* (2013.01); *A61M 2209/082* (2013.01)

(58) Field of Classification Search
CPC ... A45C 2011/002; A45C 1/06; A45C 11/182; A45C 2011/007; A45C 2011/065
USPC .................................... 206/320, 37; 224/218
See application file for complete search history.

(56) References Cited

U.S. PATENT DOCUMENTS

| | | |
|---|---|---|
| 5,054,505 A | 10/1991 | Yuhara |
| 5,176,643 A | 1/1993 | Kramer et al. |
| 5,658,259 A | 8/1997 | Pearson et al. |

| | | | |
|---|---|---|---|
| 6,595,362 B2 | 7/2003 | Penney et al. | |
| 7,390,319 B2 | 6/2008 | Friedman | |
| 7,894,095 B2 | 2/2011 | Silverbrook et al. | |
| 7,914,460 B2 | 3/2011 | Melker et al. | |
| 8,833,379 B1 | 9/2014 | Kaplan | |
| 9,138,539 B1 | 9/2015 | Friedman | |
| 9,479,212 B1 * | 10/2016 | Garcia .................... G06F 1/189 | |
| 9,590,683 B2 | 3/2017 | Greiner | |
| 9,608,686 B1 * | 3/2017 | Coulter .................. H04B 1/036 | |
| 9,913,517 B2 * | 3/2018 | Poon ....................... A45C 11/00 | |
| 9,919,106 B2 | 3/2018 | Friedman | |
| 10,022,506 B2 | 7/2018 | Pribitkin | |
| 10,728,754 B2 * | 7/2020 | Lee ......................... H04W 12/02 | |
| 11,119,544 B1 * | 9/2021 | Perez ................. H05K 7/20154 | |
| 11,147,659 B1 * | 10/2021 | Seery ................... B65D 51/248 | |
| 2005/0032482 A1 | 2/2005 | Brudos | |
| 2006/0027481 A1 | 2/2006 | Gelardi | |
| 2006/0042971 A1 | 3/2006 | Holmes | |
| 2006/0126304 A1 | 6/2006 | Smalc et al. | |
| 2007/0181425 A1 | 8/2007 | Kim | |
| 2008/0020794 A1 | 1/2008 | Garon et al. | |
| 2008/0045278 A1 | 2/2008 | Kim | |
| 2008/0166791 A1 | 7/2008 | Kim et al. | |
| 2008/0171575 A1 | 7/2008 | Choi et al. | |
| 2009/0059481 A1 * | 3/2009 | Taylor .................. H04B 1/3816 |
| | | | 361/679.01 |

(Continued)

*Primary Examiner* — King M Chu

(74) *Attorney, Agent, or Firm* — RM Reed Law PLLC

(57) ABSTRACT

Holder devices are described herein that are configured to secure auto-injection devices to a smartphone or a protective phone case. In some implementations, the device may include a body portion configured to secure an auto-injectable device and a coupling mechanism coupled to the body portion and configured to attach to one or more of a smartphone or a protective case associated with the smartphone.

18 Claims, 12 Drawing Sheets

(56)          References Cited

U.S. PATENT DOCUMENTS

| | | | |
|---|---|---|---|
| 2014/0204513 A1* | 7/2014 | Del Padre | F16M 13/00 |
| | | | 239/289 |
| 2014/0216976 A1* | 8/2014 | Conarro | H04B 1/3888 |
| | | | 206/525 |
| 2015/0233681 A1 | 8/2015 | Olah | |
| 2018/0270339 A1* | 9/2018 | Pellegrino | H04M 1/035 |
| 2019/0260411 A1* | 8/2019 | Langhans | A61M 5/002 |
| 2021/0085064 A1* | 3/2021 | Khalsa | H04M 1/04 |
| 2021/0322678 A1* | 10/2021 | Evelyn | A61M 5/3202 |
| 2022/0094383 A1* | 3/2022 | Zhang | A45C 13/04 |

* cited by examiner

200

Camera(s)
108

Smartphone
102

Rear View
106

Arms
114

Adjustment Arrows
202

Adjustment Arrows
118

Auto-Injection
Device
116

Holder
210

Body Portion
212

300

Arms
114

Adjustment Arrows
202

Adjustment Arrows
118

Auto-Injection
Device
116

Holder
210

Body Portion
212

320

Holder
210

Body Portion
212

Spacer
302

Adjustment
Arrows
118

Arms
114

Arm Slot
304

Smartphone
102

Protective Cover
602

Holder
610

Body Portion
612

Auto-Injection Device
116

Attachment Element
(e.g., Arm)
614(1)

Attachment Element
(e.g., Arm)
614(2)

600

Smartphone
102

Protective Cover
602

Holder
1010

Release Mechanism
1012

Auto-Injection
Device
116

Attachment Element
1014

1000

HOLDER TO SECURE AN AUTO-INJECTION DEVICE

FIELD

The present disclosure is generally related to auto-injection devices, such as for self-treatment of an allergic reaction or other condition. More particularly, the present disclosure is related to holders for securing auto-injection devices.

BACKGROUND

Individuals who have severe allergies or who have conditions that require frequent injections sometimes carry auto-injection devices. An example of such an auto-injection device for emergency treatment of allergic reactions (anaphylaxis) is the EPIPEN®, which is commercially available from EM Industries, Inc. of New York. Another example is the AUVI-Q®, which is commercially available from Kaleo, Inc of Virginia.

SUMMARY

Like keys, a wallet, or a smartphone, an auto-injection device is another object that a user has to keep track of when he or she is outside, at a club, at a restaurant, at an event, in school, and so on. Such objects may be a necessary inconvenience. Embodiments of a holder are described herein that is configured to secure an auto-injection device to a smartphone or to a protective case of a smartphone. In some implementations, the holder may include one or more arms or bands to couple to the smartphone or protective case. In other implementations, the holder may utilize one or more magnets, an adhesive, suction cups, or any combination thereof to secure the holder to the smartphone or protective case. The holder may provide a convenient way for a person to carry his or her auto-injection device, by coupling the device to the person's phone so that it won't be easily forgotten or lost.

In some implementations, a device may include a body portion configured to secure an auto-injectable device and a coupling element extending from the body portion. The coupling element may be configured to releasably couple to one or more of a smartphone or a protective phone case associated with the smartphone to releasably secure the body portion to the smartphone.

In other implementations, a device may include a housing and a coupling mechanism coupled to or integrated with the housing. The housing may be configured to secure an auto-injectable device. The coupling mechanism may be configured to releasably attach to one or more of a smartphone or a protective phone case associated with the smartphone. The coupling mechanism may include a magnet, an adhesive layer, a suction device (such as a suction cup), an elastic arm or band, another coupling element, or any combination thereof.

In still other implementations, a device may include a body portion configured to secure an auto-injectable device and may include one or more arms extending from the body portion. The one or more arms may be configured to releasably engage the protective phone case associated with a smartphone to releasably secure the body portion to one or more of the protective phone case or the smartphone.

In some implementations, a device may include a body portion configured to secure an auto-injectable device. The device may include a coupling element extending from the body portion and configured to engage one or more surfaces of one of a smartphone or a protective case associated with the smartphone to secure the body portion to the smartphone. The device may include one or more spacers to maintain at least one air gap between the body portion and one of the smartphone or the protective case. In some implementations, the spacers may be coupled to or integrated with the coupling element.

BRIEF DESCRIPTION OF THE DRAWINGS

The detailed description is set forth with reference to the accompanying figures. In the figures, the left most digit(s) of a reference number identifies the figure in which the reference number first appears. The use of the same reference numbers in different figures indicates similar or identical items or features.

While implementations are described in this disclosure by way of example, those skilled in the art will recognize that the implementations are not limited to the examples or figures described. It should be understood that the figures and detailed description(s) thereto are not intended to limit implementations to the particular form disclosed, but on the contrary, the intention is to cover all modifications, equivalents, and alternatives falling within the spirit and scope as defined by the appended claims. The headings used in this disclosure are for organizational purposes only and are not meant to limit the scope of the description or the claims. As used throughout this application, the word "may" is used in a permissive sense (in other words, the term "may" is intended to mean "having the potential to") instead of in a mandatory sense (as in "must"). Similarly, the terms "include", "including", and "includes" mean "including, but not limited to".

DETAILED DESCRIPTION OF ILLUSTRATIVE EMBODIMENTS

An auto-injection device, like keys, a wallet, and a smartphone, is another object that a user has to keep track of when he or she is outside, at a club, at a restaurant, at an event, in school, in a car, and so on. Embodiments of a holder are described herein that is configured to secure an auto-injection device to a smartphone or to a protective case of a smartphone. In some implementations, the holder may include one or more arms or bands to couple to the smartphone or protective case. In other implementations, the holder may utilize one or more magnets, an adhesive layer, one or more suction cups, one or more arms, or any combination thereof to secure the holder to the smartphone or protective case.

In some implementations, the holder may utilize passive cooling, such as by including one or more spacers between a body portion of the holder and the protective case or rear surface of the smartphone to provide an air gap to allow air flow between the smartphone and the holder. In some instances, passive cooling may include using phase change materials or other heat transfer materials to draw heat away from an auto-injection device. In other instances, the holder may include active cooling, such as a fan, to facilitate cooling of the auto-injection device.

The holder is a device that secures the auto-injection device and that couples to a smartphone. Since people have grown accustomed to keeping track of the whereabouts of their smartphones, coupling the auto-injection device to the smartphone makes it easier for a user to keep track of the auto-injection device. Examples of such holders are described below with respect to FIGS. 1-12.

Figure 1:
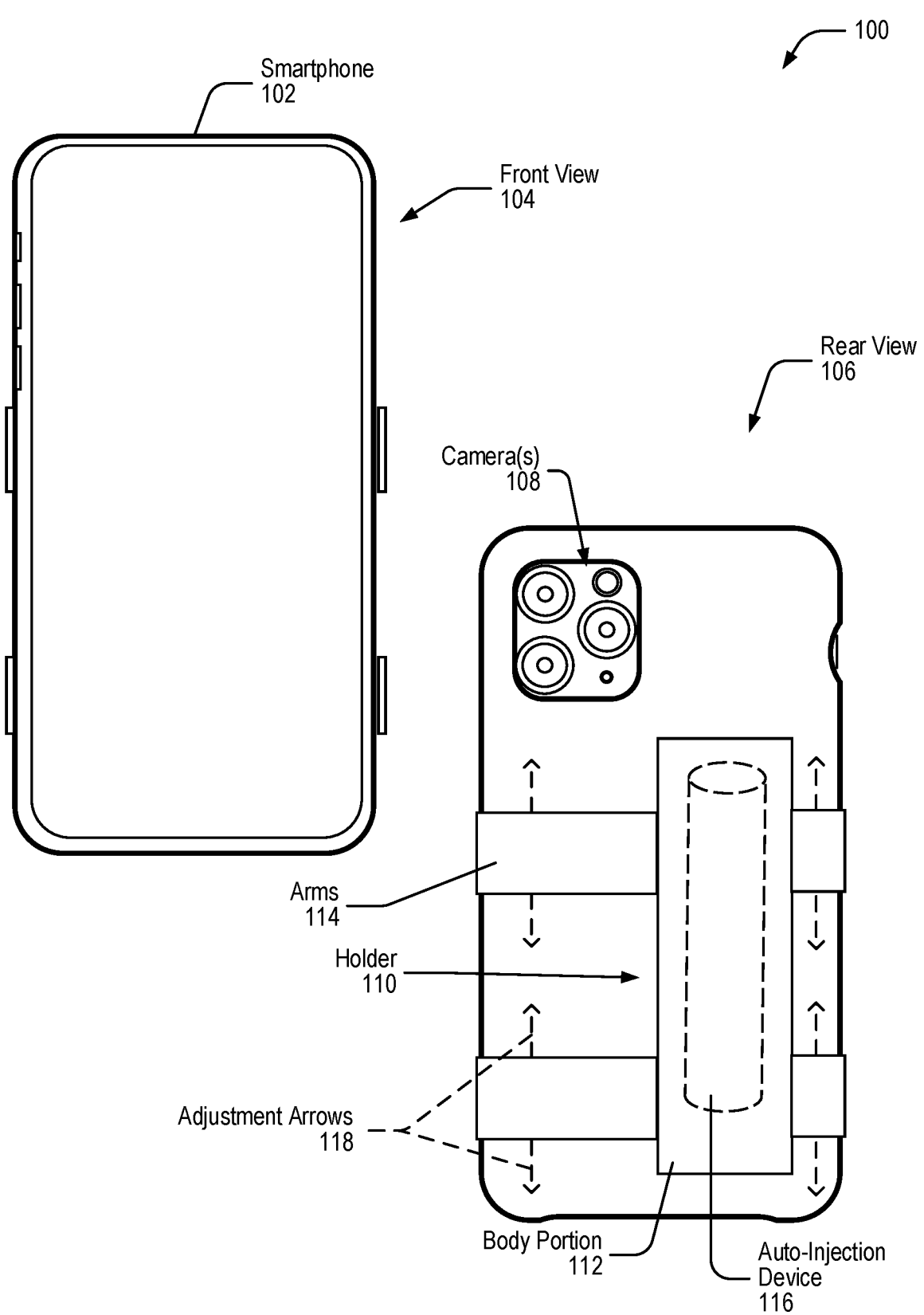
FIG. 1 depicts a smartphone and a holder including an auto-injection device coupled to the smartphone, in accordance with certain embodiments of the present disclosure.

FIG. 1 depicts a diagram 100 including a smartphone 102 and a holder 110 including an auto-injection device 118 coupled to the smartphone 102, in accordance with certain embodiments of the present disclosure. The diagram 100 includes a front view 104 and a rear view 106 of the smartphone 102. The rear view 106 shows one or more cameras 108, which can be seen through one or more of the housing of the smartphone 102 or through an opening of a protective cover of the smartphone 102.

The holder 102 may include a body portion 112, which may include an enclosure configured to secure an auto-injection device 116. In some implementations, the body portion 112 may secure the auto-injection device 116 by pressing the auto-injection device 116 against a rear surface of the smartphone 102. The holder 102 may further include one or more coupling elements, such as one or more arms 114, extending from the body portion. The one or more arms 114 may releasably engage the edges of one or more of the smartphone 102 or a protective cover of the smartphone 102. In some implementations, the arms 114 may be adjustable as indicated by the adjustment arrows 118. In other implementations, the length of the arms 114 may be adjustable or the arms 114 may be interchangeable so that the holder 110 may be used with different smartphones 102.

In some implementations, the one or more arms 114 may apply a compression force to the one or more edges of the smartphone or the protective phone case to releasably secure the body portion 112. While the illustrated example of FIG. 1 includes arms 114, the coupling element may be implemented as a loop that is configurable to fit over at least one of the one or more edges.

The body portion 112 may be formed from a first material, and the one or more arms 114 may be formed from a second material. In one example, the first material of the body portion 112 may be more elastic (may have a higher modulus of elasticity) than the second material of the arms 114. In another example, the second material of the arms 114 may be more elastic (may have a higher modulus of elasticity) than the first material of the body portion 112.

In some implementations, the body portion 112 may provide thermal management to prevent the auto-injection device 116 from exceeding a pre-determined temperature. The thermal management may be provided by passive features, such as one or more spacers positioned between the body portion 112 and a rear surface of the smartphone 102 to allow airflow between the smartphone 102 and the holder 112. In other implementations, the thermal management may be provided using phase change materials or by forming the body portion 112 from material that may draw heat away from the auto-injection device 116. In still other implementations, the thermal management may be provided by one or more of an airflow path or a fan to direct air over the auto-injection device 116 along the airflow path. Other implementations are also possible.

Depending on the implementation, the body portion 112 of the holder may define an enclosure sized to receive a protective cover for the auto-injection device 116. The body portion 112 and the protective cover may protect the auto-injection device 116 from impacts.

In some implementations, in addition to or in lieu of the arms 114, the coupling mechanism may include one or more of an adhesive, a suction cup, or a magnet, which may releasably attach or which may reinforce the releasable attachment to the smartphone 102 or the smartphone cover.

In some implementations, the holder 110 may include a release mechanism coupled to the body portion 112 and configured to eject the auto-injection device 116. The release mechanism may include one or more of a button, a cover, or a switch that may allow access to the auto-injection device 116 in response to user-selection of the release mechanism.

Figure 2:
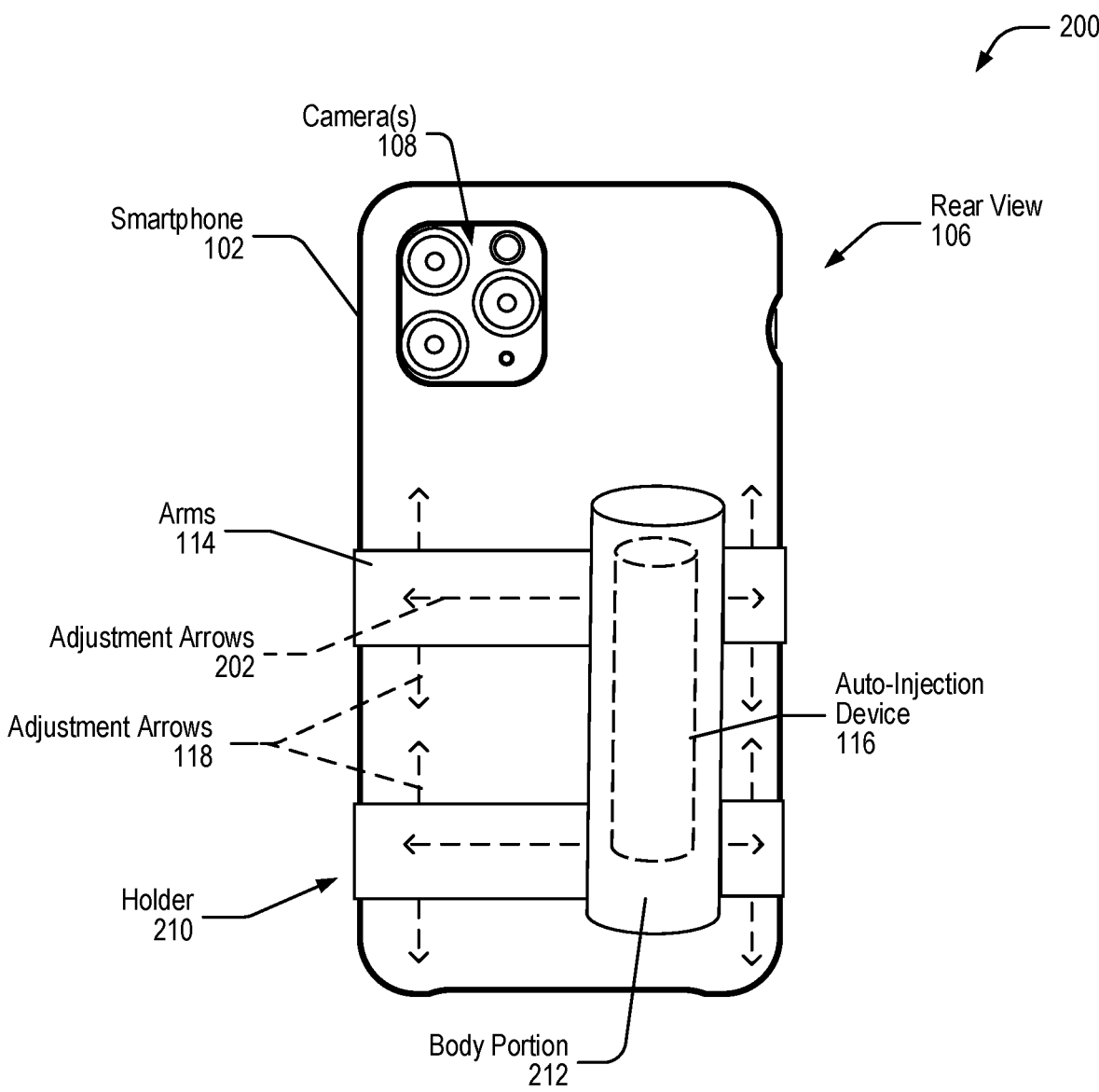
FIG. 2 depicts a smartphone and a holder coupled to the smartphone and including a cylindrical body portion to secure an auto-injection device, in accordance with certain embodiments of the present disclosure.

FIG. 2 depicts a diagram 200 including a smartphone 102 and a holder 110 coupled to the smartphone 102 and including a cylindrical body portion 212 to secure an auto-injection device 116, in accordance with certain embodiments of the present disclosure. The holder 210 may include all the elements of the holder 110 of FIG. 1 or any of the variations described above.

In this example, the body portion 212 of the holder 210 is implemented as a cylindrical shape, in contrast to the rectangular shape of the holder 110 in FIG. 1. The body portion 212 may be selected based on the shape of the auto-injection device 116. In this case, the auto-injection device 116 is cylindrical, so the body portion 212 is cylindrical. In alternative implementations, the auto-injection device 116 may have a different shape, and the body portion 212 may have a different shape or may otherwise be configured to receive the auto-injection device 116.

While, in this example, the body portion 212 is shown as being coupled to the smartphone 102 along a rear surface of the smartphone 102, in some implementations, the attachment mechanisms (such as the one or more arms 114) may secure the body portion 212 along an edge of the smartphone 102. The arms 114 may also be moved up or down so that the arms 114 do not obscure the cameras 108. Additionally, in some implementations, the body portion 212 may slide back and forth as indicated by arrows 202.

Figure 3A:
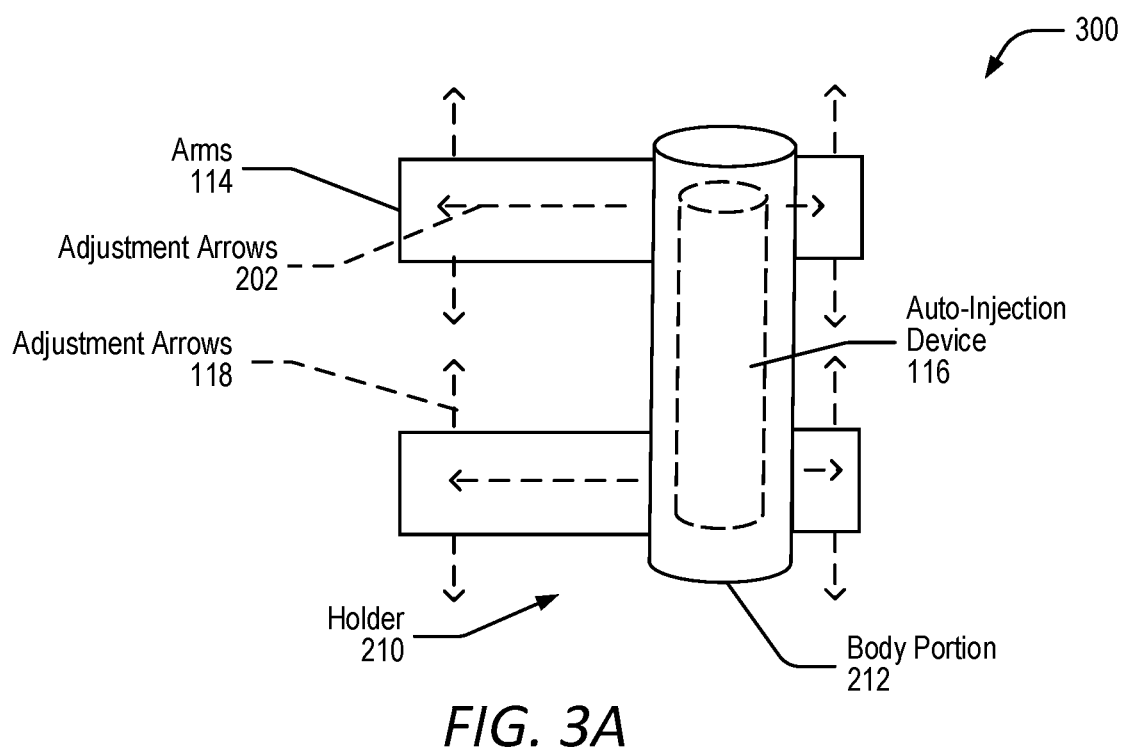
FIGS. 3A and 3B depict a cylindrical holder including adjustable arms to couple the holder to a smartphone or to a protective cover of a smartphone and including spacers to provide an air gap for cooling air flow, in accordance with certain embodiments of the present disclosure.
Figure 3B:
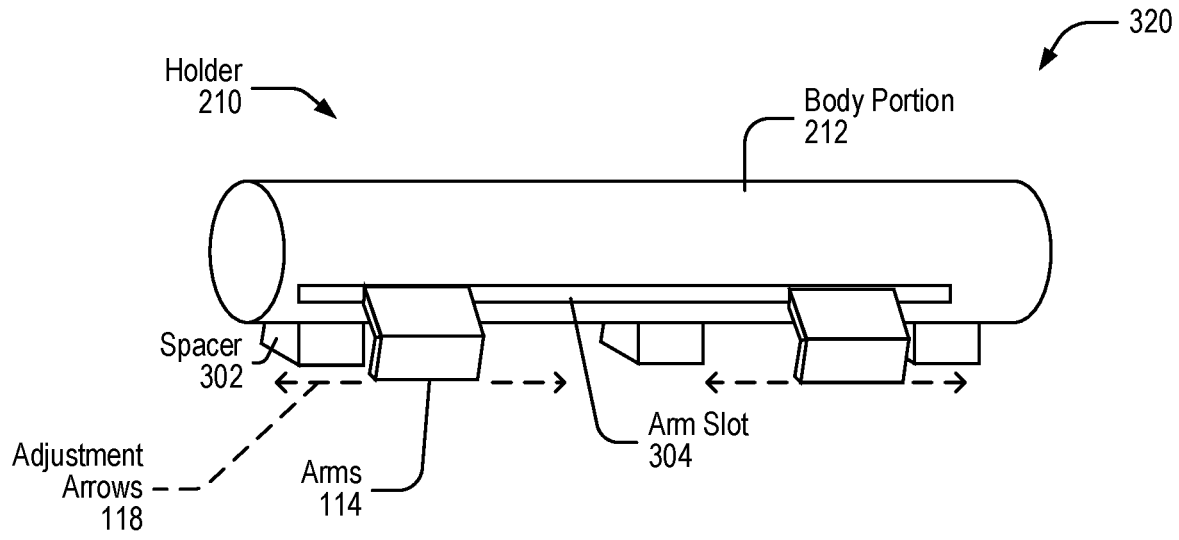

FIGS. 3A and 3B depict diagrams 300 and 320, respectively, including a cylindrical holder 210 including adjustable arms 114 to couple the holder 210 to a smartphone 102 or a protective cover of a smartphone 102, in accordance with certain embodiments of the present disclosure. The examples depicted in FIGS. 3A and 3B may be an implementation of the holder 210 of FIG. 2 separated from the smartphone 102.

In FIG. 3A, the diagram 300 shows a top view of the holder 210 including a body portion 212 and arms 114 extending from the body portion 212, which is securing the auto-injection device 116. In this example, the arms 114 may be shifted up or down by the user, as indicated by the arrows 118. Additionally, the body portion 212 may be moved back and forth along the arms 114, as indicated by the arrows 202.

In FIG. 3B, the diagram 320 shows a side view of the body portion 212 of the holder 210. In this example, the body portion 212 includes an opening or arm slot 304 within which the arms 114 may move back and forth as indicated by the adjustment arrows 118.

In this example, the body portion 212 may be separated from the rear surface of the smartphone 102 or the protective cover of the smartphone 102 by one or more spacers 302. The spacers 302 may provide air gaps to allow air flow between the smartphone 102 and the body portion 212 to provide passive cooling of the holder 210 and an auto-injection device 116 within the body portion 212.

Figure 4:
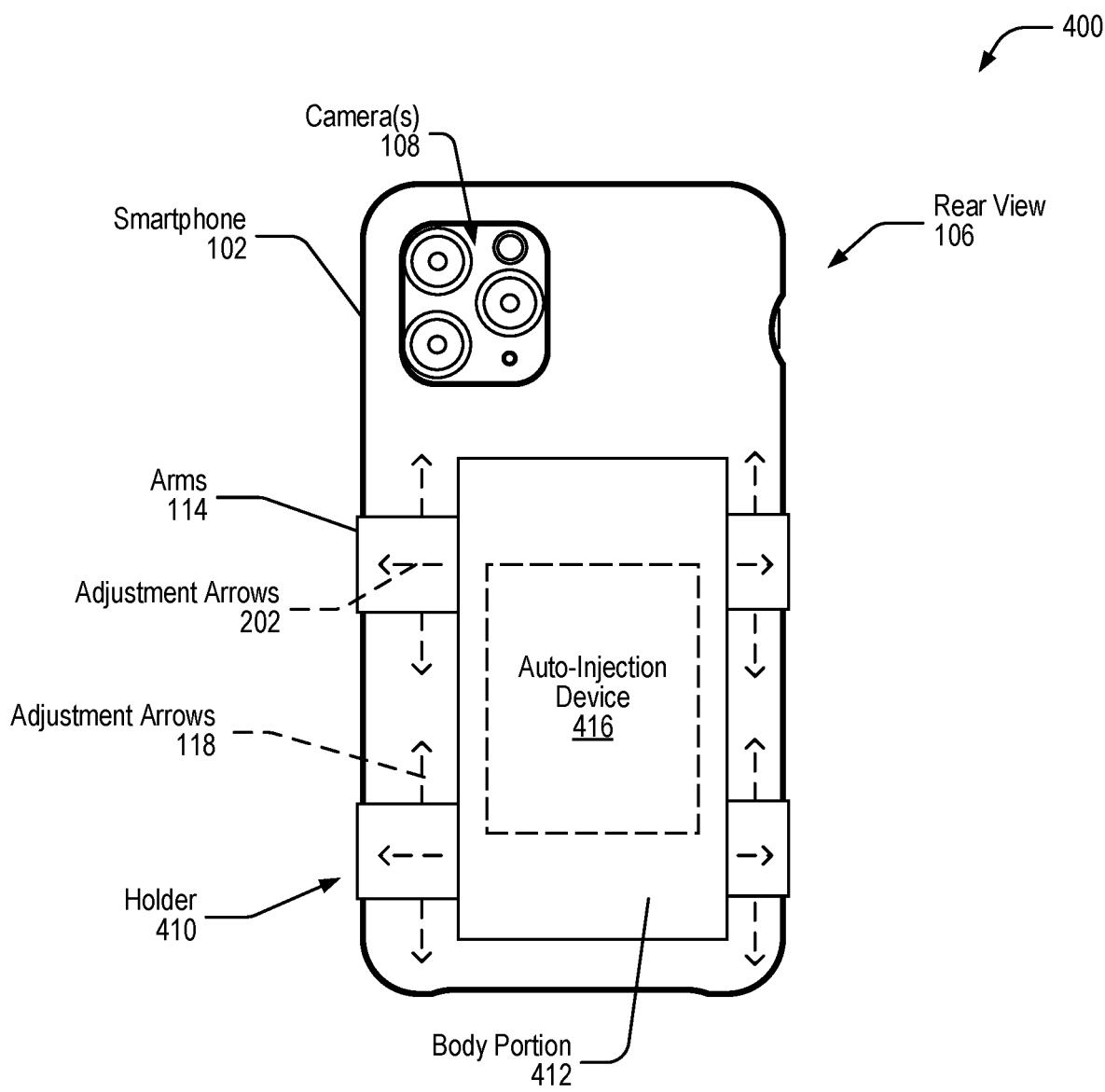
FIG. 4 depicts a smartphone and a holder coupled to the smartphone and including a rectangular body portion to secure an auto-injection device, in accordance with certain embodiments of the present disclosure.

FIG. 4 depicts a diagram 400 including a smartphone 102 and a holder 410 coupled to the smartphone 102 and including a rectangular body portion 412 to secure an auto-injection device 416, in accordance with certain embodiments of the present disclosure. The holder 410 may include all the elements of the holder 110 in FIG. 1 or the holder 210 in FIG. 2, except that the body portion 412 is rectangular.

In this example, the holder 410 may include the arms 114, which may releasably couple the body portion 412 to the smartphone 102. The arms 114 may be adjusted as indicated by the adjustment arrows 118, and the body portion 410 may be moved along the arms 114 as indicated by the adjustment arrows 202.

Figure 5:
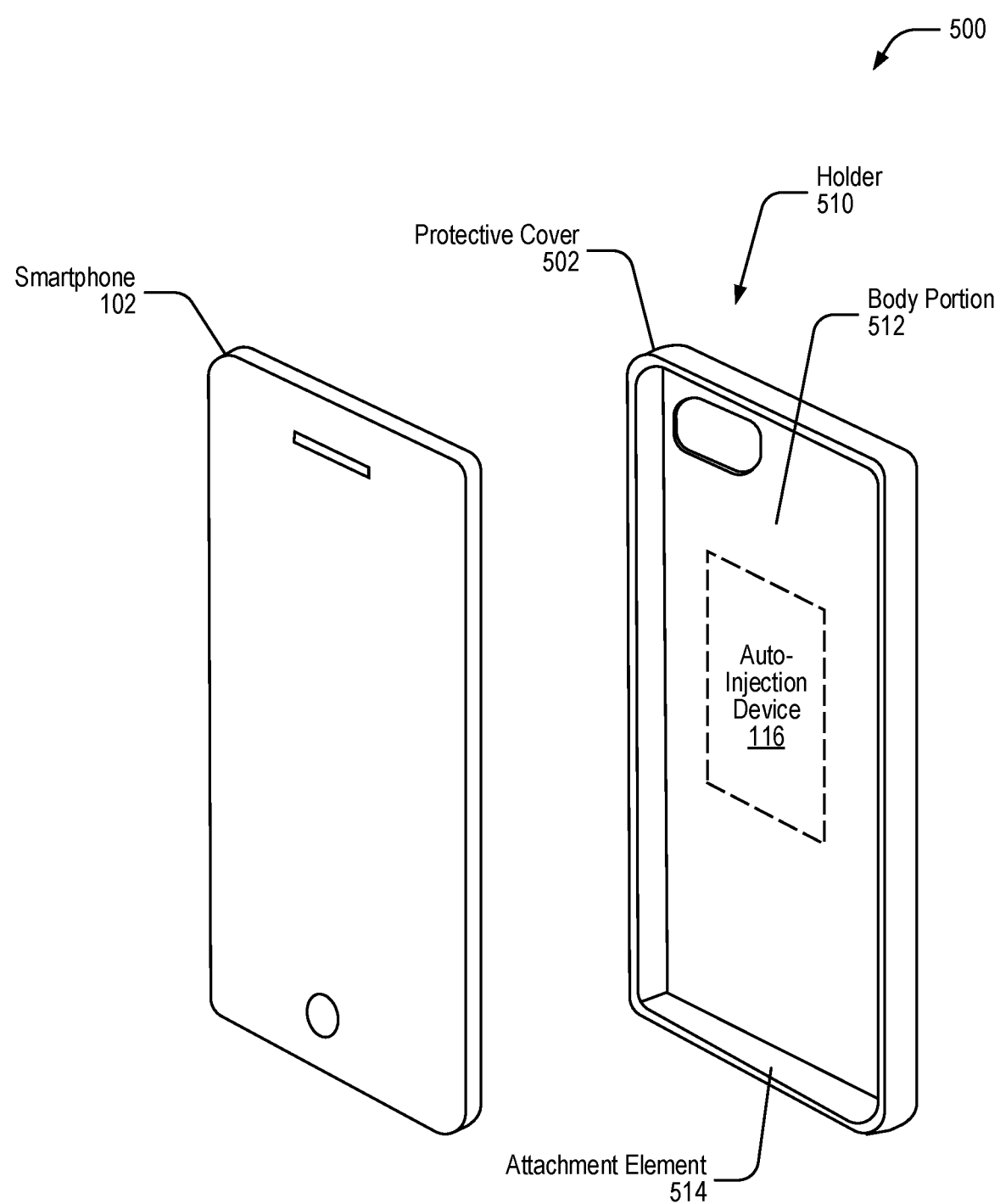
FIG. 5 depicts a smartphone and a protective cover with an integrated holder to secure an auto-injection device, in accordance with certain embodiments of the present disclosure.

FIG. 5 depicts a diagram 500 including a smartphone 102 and a protective cover 502 with an integrated holder 510 to secure an auto-injection device 116 (or 416), in accordance with certain embodiments of the present disclosure. The holder 502 may include a body portion 512 and an attachment element 514, which may extend from the body portion 512. In this example, the attachment element 514 may extend around the edges of the smartphone 102 and may be configured to releasably secure the holder 502 to the smartphone 102 using a hoop stress, compressing the attachment element 514 around the edges of the smartphone 102.

It should be appreciated that, in this example, the legs 114 may be replaced with at least one leg or sidewall to couple the protective cover 502 to the smartphone 102. Other implementations are also possible.

Figure 6:
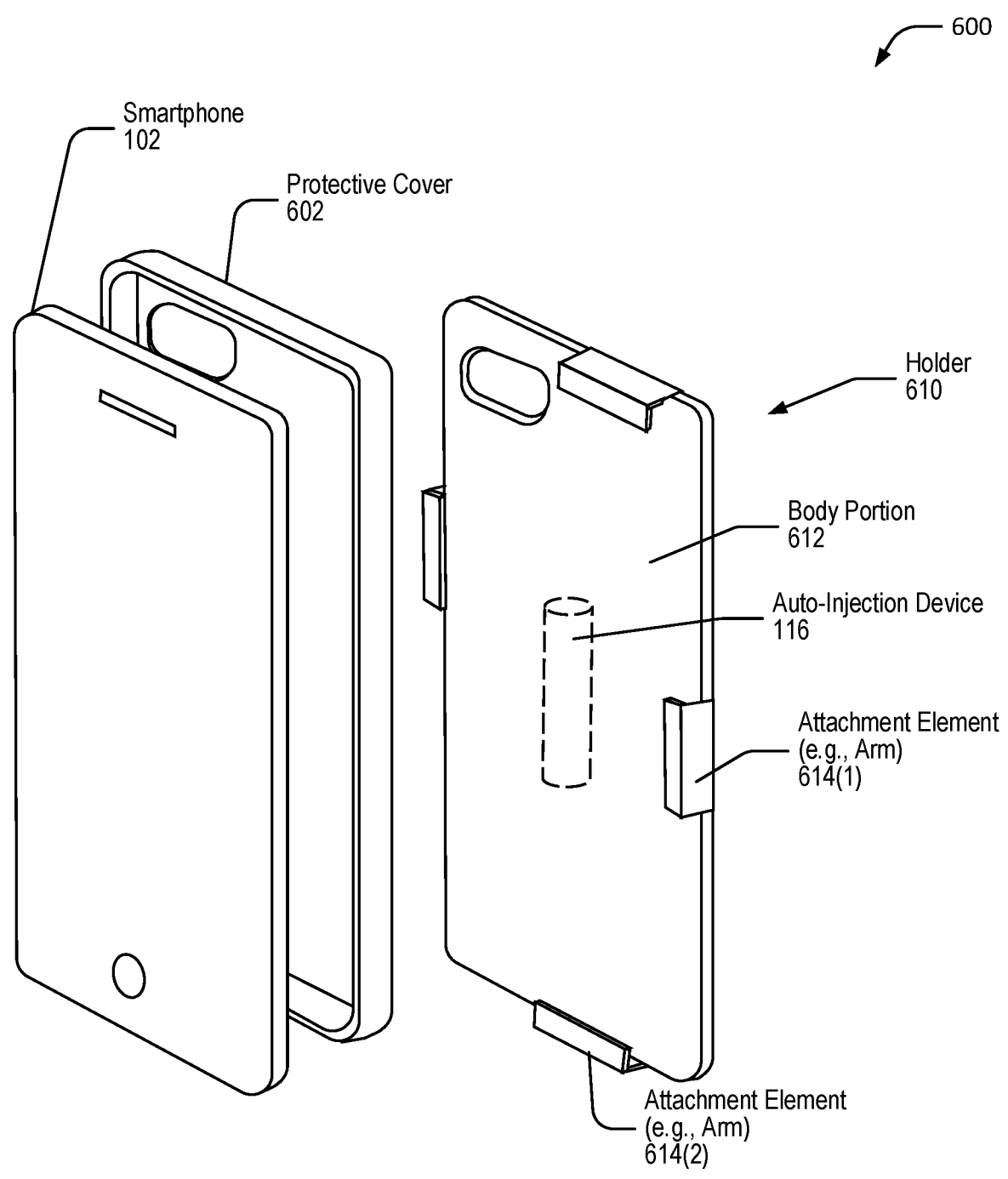
FIG. 6 depicts a smartphone, a protective cover, and a holder with arms configured to secure an auto-injection device to one or more of the smartphone or the protective cover, in accordance with certain embodiments of the present disclosure.

FIG. 6 depicts a diagram 600 including a smartphone 102, a protective cover 602, and a holder 610 with attachment elements 614 (e.g., arms) configured to secure the holder 610 to one or more of the smartphone 102 or the protective cover 602, in accordance with certain embodiments of the present disclosure. The holder 610 may include a body portion 612 to secure the auto-injection device 116 to the smartphone 102.

In some implementations, the body portion 612 may be more elastic than the arms 614 and may stretch around the auto-injection device 116 to secure the auto-injection device 116 to the smartphone 102. Alternatively, the body portion 612 may include an enclosure sized to receive the auto-injection device 116. Additionally, while the auto-injection device 116 is depicted as a cylindrical device, in other implementations, the injection device 116 may have a rectangular shape or another shape. Other implementations are also possible.

Figure 7:
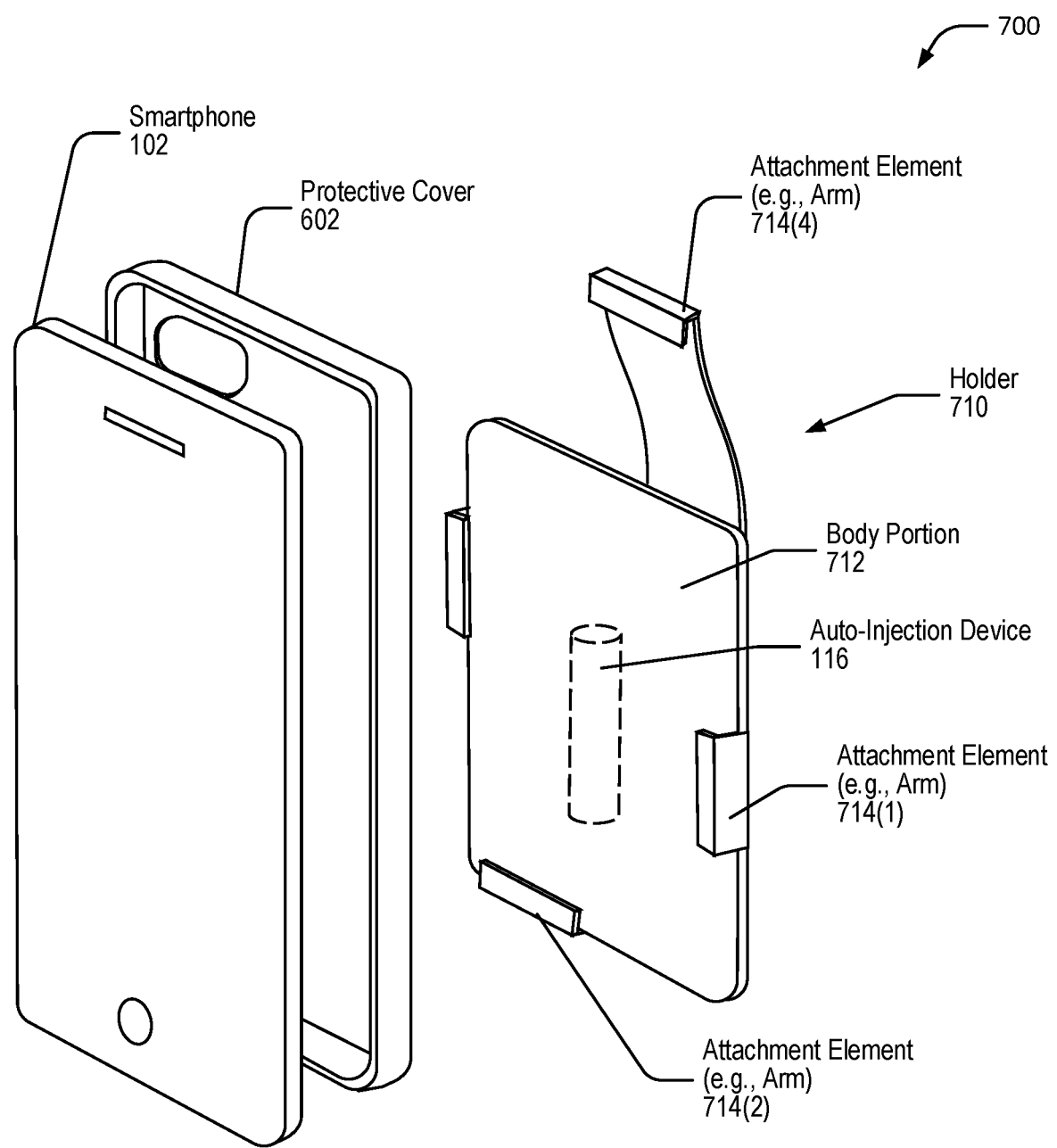
FIG. 7 depicts a smartphone, a protective cover, and a holder with arms configured to secure an auto-injection device to one or more of the smartphone or the protective cover, in accordance with certain embodiments of the present disclosure.

FIG. 7 depicts a diagram 700 including a smartphone 102, a protective cover 602, and a holder 710 with arms 714 configured to secure an auto-injection device 116 to one or more of the smartphone 102 or the protective cover 602, in accordance with certain embodiments of the present disclosure. The holder 710 may include any of the elements described above with respect to the holders 110, 210, 410, 510, or 610.

In this example, the body portion 712 may be shorter than the length of the protective cover 602. In this example, the arm 714(4) may be longer than the other arms 714(1) and 714(2), so that the arms 714 may cooperate to releasably secure the body portion 712 to the smartphone 102 or the protective case 602.

Figure 8:
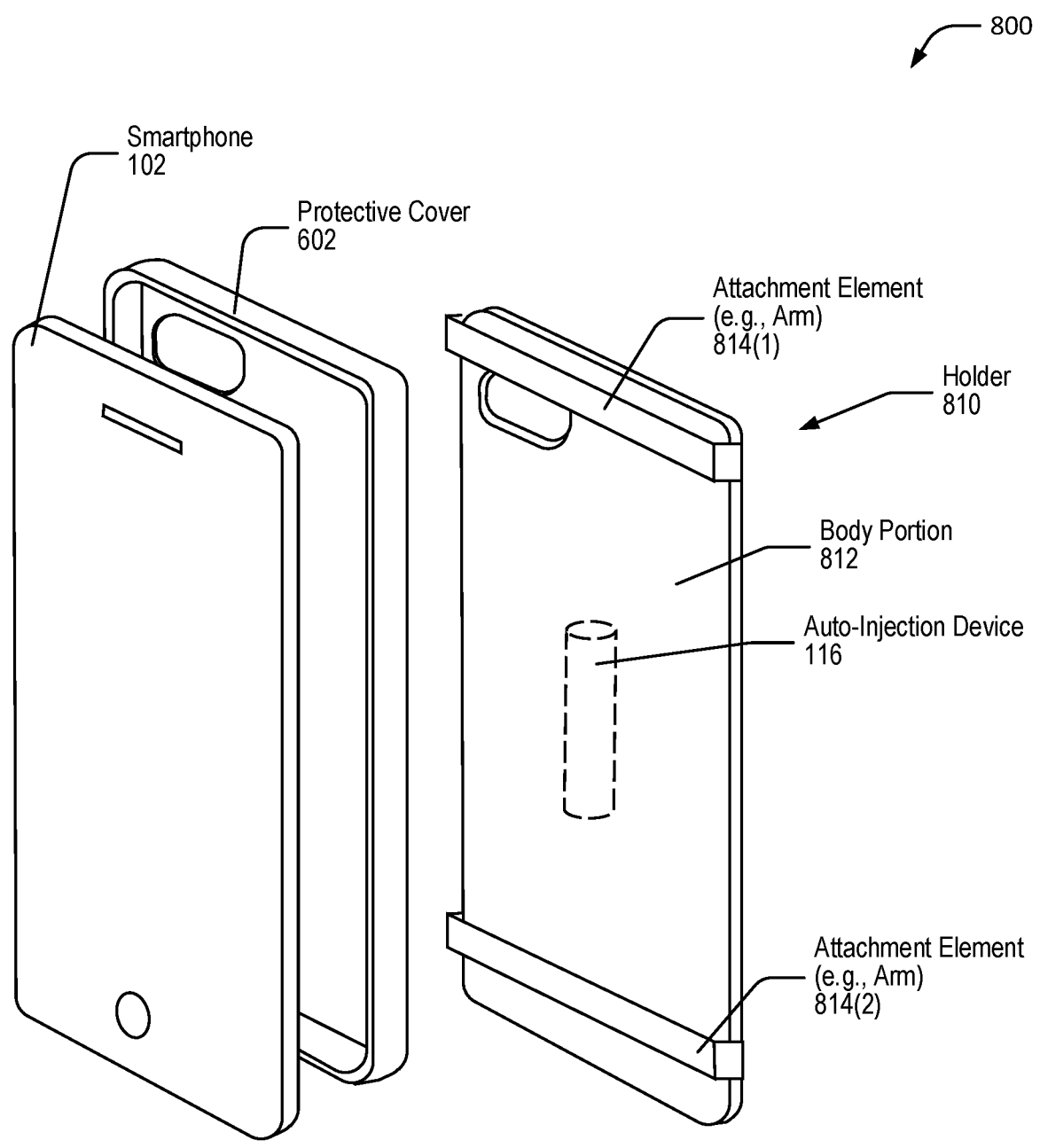
FIG. 8 depicts a smartphone, a protective cover, and a holder with loops configured to secure an auto-injection device to one or more of the smartphone or the protective cover, in accordance with certain embodiments of the present disclosure.

FIG. 8 depicts a diagram 800 including a smartphone 102, a protective cover 602, and a holder 810 with attachment elements 814 (e.g., loops) configured to secure an auto-injection device 116 to one or more of the smartphone 102 or the protective cover 602, in accordance with certain embodiments of the present disclosure.

In this example, the attachment elements 814 may be more elastic and flexible than the body portion 812. Alternatively, the attachment elements 814 and the body portion 812 may be formed from the same material and may have the same elasticity. Other implementations are also possible.

Figures 9A, 9B, 9C:
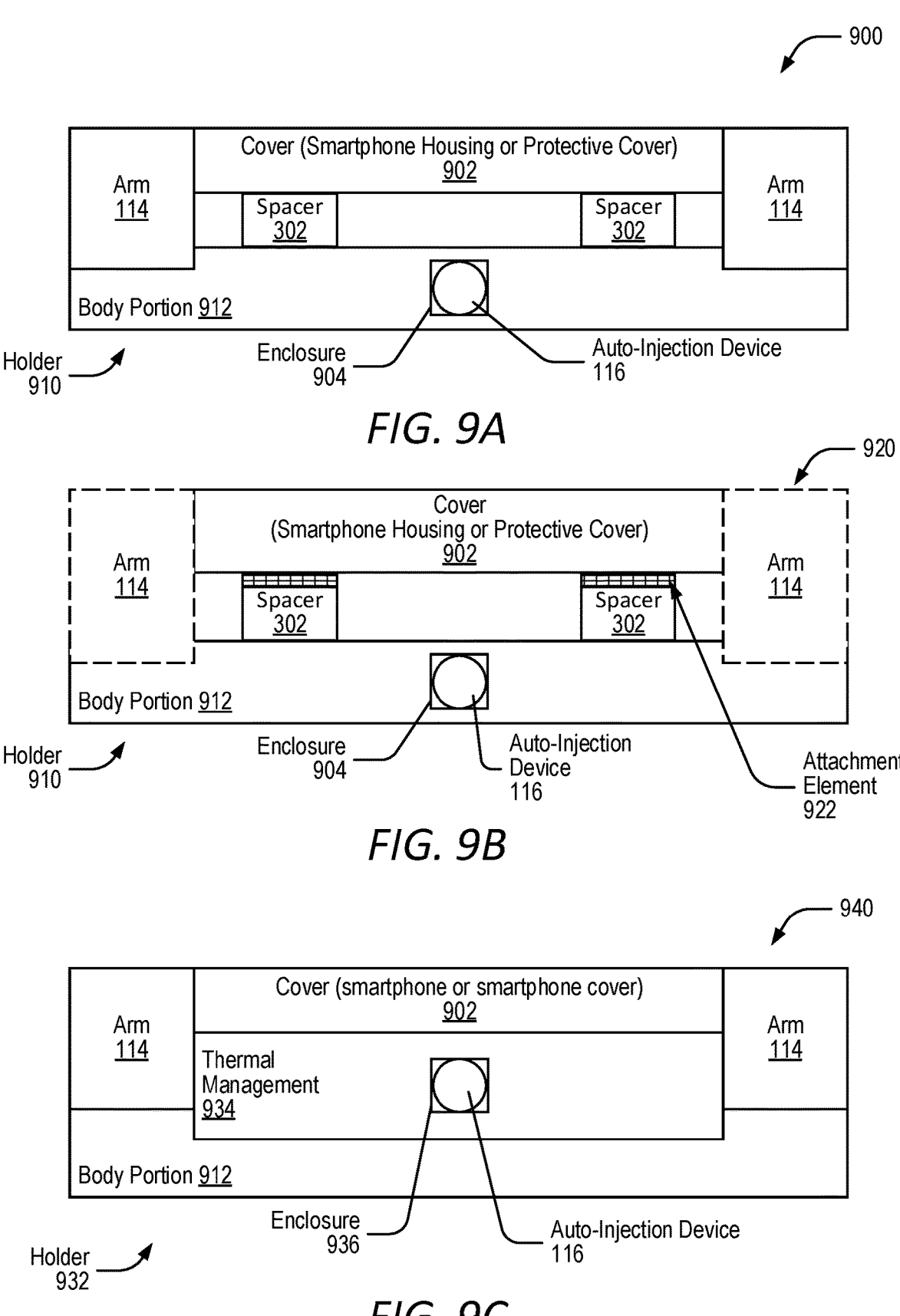
FIGS. 9A-9C depict block diagrams of a cover and a holder coupled to the cover, in accordance with certain embodiments of the present disclosure.

FIGS. 9A-9C depict block diagrams 900, 920, and 940 of a cover and a holder coupled to the cover, in accordance with certain embodiments of the present disclosure. In FIG. 9A, the diagram 900 depicts a cover 902 coupled to holder 910 including a body portion 912. The cover 902 may represent the casing or housing of a smartphone 102 or a protective cover or phone case.

The body portion 912 may include an enclosure 904 sized to receive an auto-injection device 116. While the auto-injection device 116 is depicted as a cylindrical shape, the enclosure 904 may be sized to receive auto-injection devices of different shapes and profiles.

The body portion 912 may be coupled to the cover 902 by one or more arms 114. In this example, the body portion 912 may be separated from the cover 902 by one or more spacers 302, defining an air gap between the cover 902 and the body portion 912. The air gap may allow for air flow between the cover 902 and the body portion 912.

In FIG. 9B, the diagram 920 depicts a cover 902 coupled to a body portion 912. In this example, the body portion 912 may include one or more spacers 302 which may include an attachment element 922 that may couple the body portion 912 to the cover 902. The attachment element 922 may include an adhesive layer, a magnet, a suction cup, or another element to couple the end of the spacer 302 to the cover 902. The body portion 912 may be coupled to arms 114, which may also releasably couple to the cover 902. In this example, the arms 114 are shown in phantom to indicate that they may be omitted in some implementations.

In FIG. 9C, the diagram 940 depicts a cover 902 coupled to a holder 932 having a body portion 912, which may include or may be coupled to thermal management 934. In this example, thermal management may include passive thermal management configured to maintain a temperature of the auto-injection device 116 at or below a selected temperature level. In some implementations, the thermal management 934 may include air gaps, phase change materials, heat sinks, heat transfer materials, or any combination thereof selected to draw heat away from the enclosure 936 that holds the auto-injection device 116. In other implementations, the thermal management 934 may include air gaps, a fan, other cooling elements, or any combination thereof, which may be configured to maintain a temperature of the enclosure 936 at or below a selected temperature.

It should be understood that the attachment element 922 in FIG. 9B may be used in conjunction with any of the holders described above with respect to FIGS. 1-9C, with or without the arms 114. Additionally, it should be appreciated that the thermal management 934 may be incorporated into any of the holders described above with respect to FIGS. 1-9C.

Figure 10:
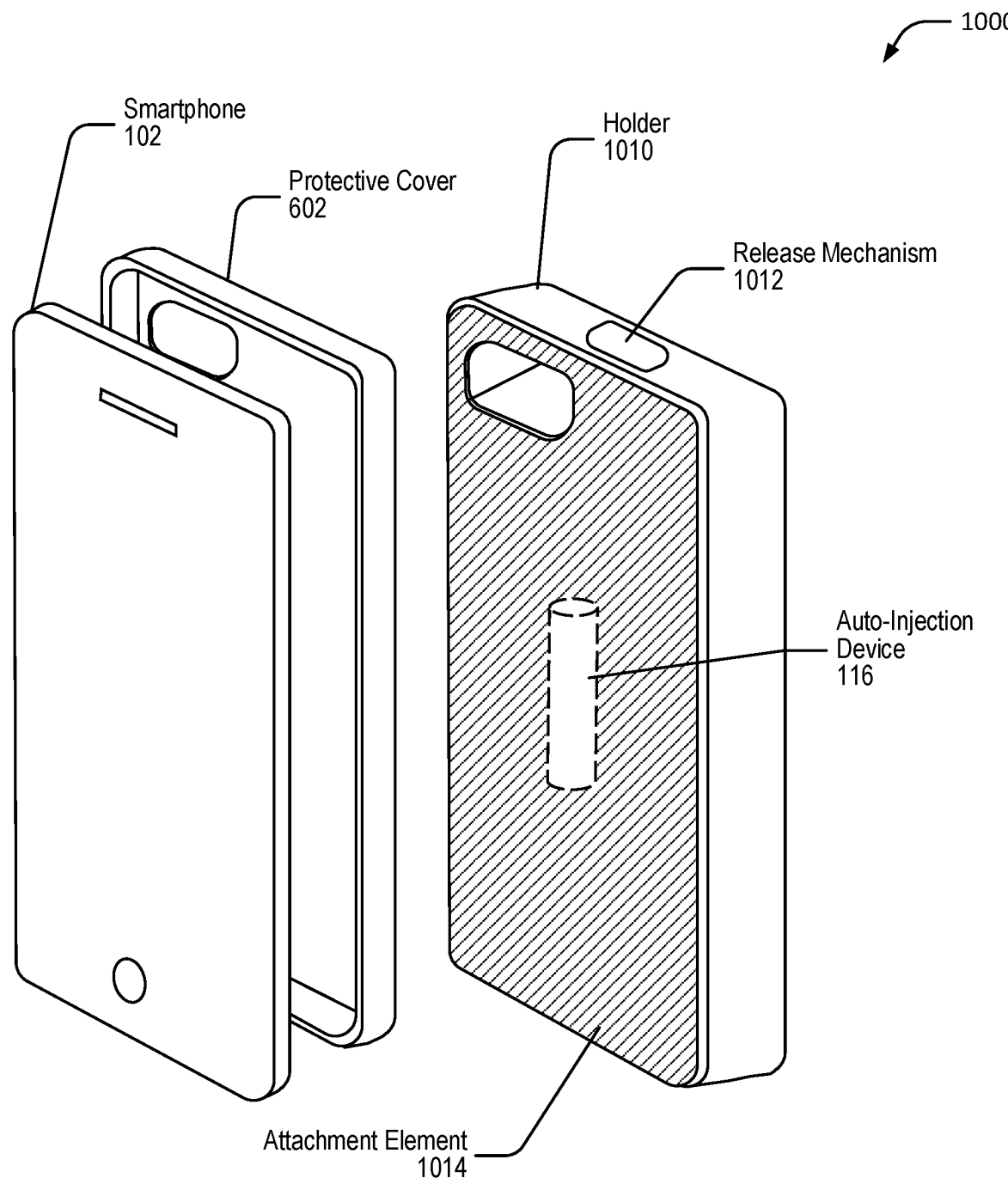
FIG. 10 depicts a diagram of a smartphone, a protective cover, and a holder including an attachment element and a release mechanism, in accordance with certain embodiments of the present disclosure.

FIG. 10 depicts a diagram 1000 of a smartphone 102, a protective cover 602, and a holder 1010 including an attachment element 1014 and a release mechanism 1012, in accordance with certain embodiments of the present disclosure. In this example, the holder 1010 is thicker and larger than some of the holders described above with respect to FIGS. 1-9C; however, the holder 1010 may have approximately the same width and height dimensions as the smartphone 102. The holder 1010 may include spacers 302 or other features described above with any of the FIGS. 1-9C, depending on the implementation.

In this example, the holder 1010 may define an enclosure sized to receive the auto-injection device 116. While the auto-injection device 116 is depicted as a cylindrical device, other shapes are also possible. The auto-injection device 116 is shown in phantom to indicate that it may be enclosed within the holder 1010. While the auto-injection device 116 is shown as substantially centered within the holder 1010, the auto-injection device 116 may be positioned near one or more of the edges.

The release mechanism 1012 may be a button or a releasable cover coupled to an edge of the holder 1010. In response to user-selection of the release mechanism 1012, the auto-injection device 116 may be ejected from or released from the holder 1010. In an example, the enclosure defined by the holder 1010 may include a spring or an elastic element configured to push the auto-injection device 116 from within the enclosure in response to user interaction with the release mechanism 1012. In an implementation, the release mechanism 1012 may include a cover that compresses the auto-injection device 116 against the spring or the elastic element such that opening of the cover ejects at least a portion of the auto-injection device 116 to enable access.

In this example, the holder 1010 may include an attachment element 1014, which may couple the holder 1010 to one or more of the protective cover 602 or the smartphone 102. In this example, the attachment element 1014 may include an adhesive layer, a magnetic layer, a suction layer, or any combination thereof. The attachment element 1014 may couple the holder 1010 to the smartphone 102 or the protective cover 602.

Figure 11:
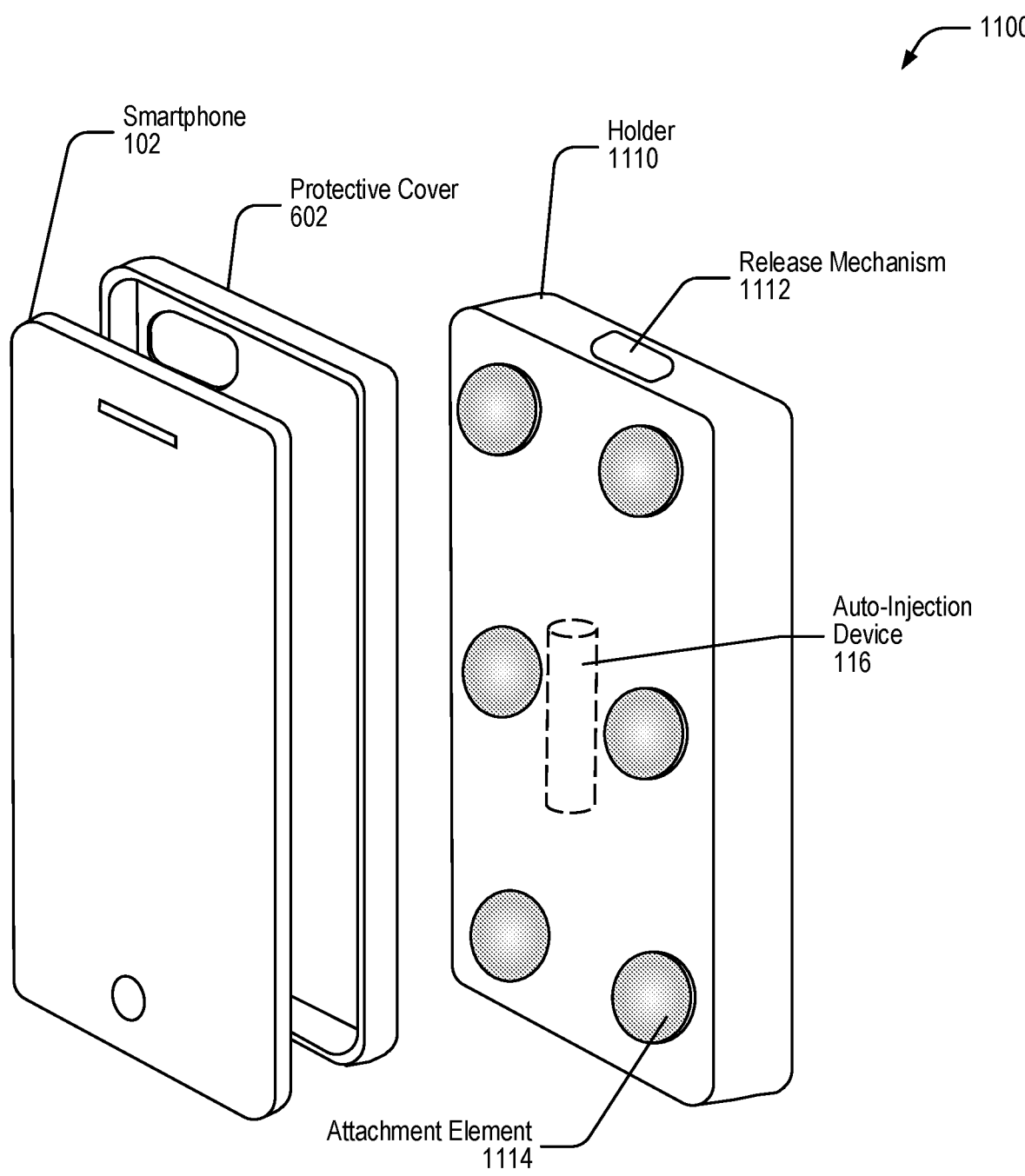
FIG. 11 depicts a diagram of a smartphone, a protective cover, and a holder including an attachment element and a release mechanism, in accordance with certain embodiments of the present disclosure.

FIG. 11 depicts a diagram 1100 of a smartphone 102, a protective cover 602, and a holder 1110 including an attachment element 1114 and a release mechanism 1112, in accordance with certain embodiments of the present disclosure. In this example, holder 1110 may include thermal management 934 and may include a spring or other feature to eject the auto-injection device 116 in response to selection of the release mechanism 1112. As previously mentioned, the enclosure may include a spring or elastic element that may be compressed between the auto-injection device 116 and the release mechanism 112 such that selection of the release mechanism 112 may cause the spring or elastic element to push the auto-injection device 116 at least partially out of the enclosure to enable access. In some implementations, the holder 1110 may be reloadable so that the holder 1110 may be reused.

In this example, the holder 1110 may include one or more attachment elements 1114, such as suction cups, to secure the holder 1110 to one of the protective cover 602 or the smartphone 102. Alternatively, the attachment elements 1114 may include one or more magnets, adhesive strips or circles, or other attachment mechanisms.

Figure 12:
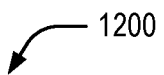
FIG. 12 depicts a block diagram of a holder device including an active thermal management feature, in accordance with certain embodiments of the present disclosure.
Figure 12:
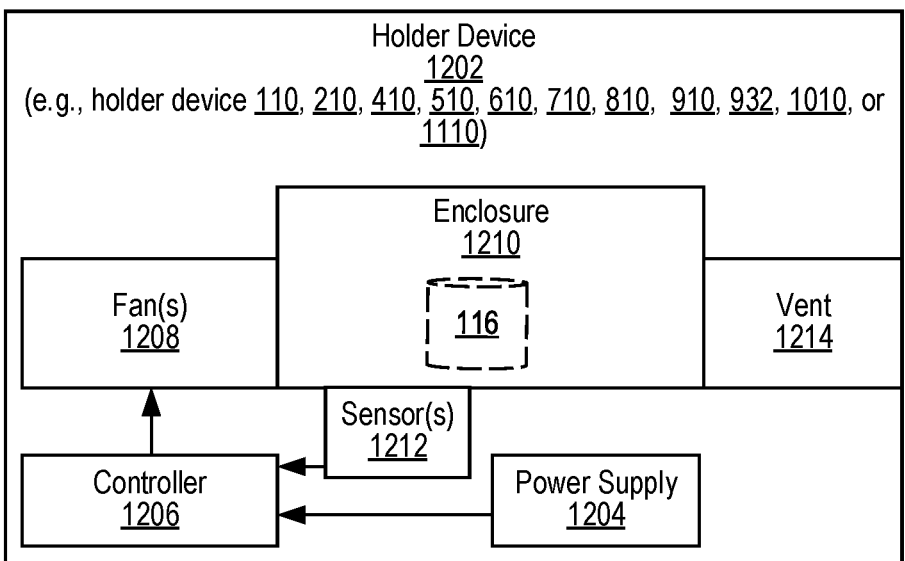

FIG. 12 depicts a block diagram 1200 of a holder device 1202 including an active thermal management feature, in accordance with certain embodiments of the present disclosure. The holder device 1202 may be an implementation of one of the holder devices 110, 210, 410, 510, 610, 710, 810, 910, 932, 1010, or 1110 of any of FIGS. 1-11.

In the illustrated example, the holder device 1202 may include a power supply 1204 configured to provide power to one or more of the components. The power supply 1204 may be a rechargeable battery.

The holder device 1202 may include a controller 1206 configured to receive power from the power supply 1204 and temperature signals from one or more sensors 1212. In response to the temperature signals, the controller 1206 may control one or more fans 1208 to direct air flow through the enclosure 1210 across the auto-injection device 116 and out a vent 1214 to maintain a selected temperature. Other implementations are also possible.

In conjunction with the devices described above with respect to FIGS. 1-12, a holder device is described that may be configured to secure an auto-injection device and that may be configured to releasably attach to one of a smartphone and a phone case. The holder device may include one or more attachment elements (arms, loops, magnets, adhesives, suction cups, other attachment features, or any combination thereof) to releasably attach the holder device to the smartphone or phone case.

The holder devices described above provide a number of advantages over conventional auto-injection devices. First, the holder attaches to a smartphone or smartphone's protective cover so that the user need only keep track of his or her smartphone and does not separately have to remember to pick up his or her auto-injection device. Second, the holder may provide supplemental protection for the smartphone, in case the user drops the smartphone. Third, the holder may provide passive cooling to prevent the medical dosage from being heated by the smartphone. Other advantages may be readily understood by reviewing the disclosure.

Although the present invention has been described with reference to preferred embodiments, workers skilled in the art will recognize that changes may be made in form and detail without departing from the scope of the invention.

What is claimed is:

1. A device comprising:

a body portion configured to secure an auto-injectable device;

a coupling element extending from the body portion and configured to engage one or more surfaces of one of a smartphone or a protective case associated with the smartphone to secure the body portion to the one of the smartphone or the protective case outside of the protective case;

one or more spacers to maintain at least one air gap between the body portion and the one of the smartphone or the protective case, the one or more spacers configured to enable air flow between the body portion and the one of the smartphone or the protective case to draw heat away from the auto-injectable device; and a release mechanism coupled to the body portion and configured to eject the auto-injectable device from the body portion in response to selection of the release mechanism.

2. The device of claim 1, wherein the coupling element includes one or more magnets to secure the body portion to the one of the smartphone or the protective case.

3. The device of claim 1, wherein the coupling element includes an adhesive layer to secure the body portion to the one of the smartphone or the protective case.

4. The device of claim 1, wherein the coupling element includes one or more arms configured to releasably engage edges of one or more of the smartphone or the protective case.

5. A device comprising:

a body portion configured to secure an auto-injectable device, the body portion including a release mechanism configured to eject the auto-injectable device from the body portion in response to selection of the release mechanism;

a coupling element extending from the body portion, the coupling element configured to secure the body portion to an exterior surface of a protective case of a smartphone; and one or more spacers to provide at least one air gap between the body portion and the exterior surface of the protective case.

6. The device of claim 5, wherein the coupling element applies a compression force to one or more edges of the protective case to secure the body portion.

7. The device of claim 6, wherein the coupling element includes a loop that is configurable to fit over at least one of the one or more edges.

8. The device of claim 5, wherein:

the coupling element further includes one or more arms coupled to the body portion;

the body portion is formed from a first material; and the one or more arms are formed from a second material.

9. The device of claim 8, wherein:

the first material has a first modulus of elasticity; and the second material has a second modulus of elasticity.

10. The device of claim 5, wherein the body portion provides thermal management to prevent the body portion from exceeding a pre-determined temperature.

11. The device of claim 10, wherein the body portion includes a fan to provide the thermal management.

12. The device of claim 5, wherein the body portion defines an enclosure, the device further comprising:

a protective cover for the auto-injectable device, the protective cover configured to secure and protect the auto-injectable device; and wherein the enclosure is sized to receive the protective cover.

13. The device of claim 5, further comprising:

a second coupling element between one or more of the body portion or the one or more spacers and a surface of the protective case; and wherein the second coupling element comprises one or more of an adhesive layer, a suction cup, or a magnet.

14. The device of claim 5, further comprising a release mechanism coupled to the body portion and configured to eject the auto-injectable device from the body portion in response to selection of the release mechanism.

15. A device comprising:

a body portion configured to secure an auto-injectable device;

a coupling mechanism coupled to the body portion and configured to attach to a protective phone case that is coupled to a smartphone;

one or more spacers configured to fit between the body portion and an exterior surface of the protective phone case to enable air flow between the auto-injectable device and the protective phone case; and a release mechanism coupled to the body portion and configured to eject the auto-injectable device from the body portion in response to selection of the release mechanism.

16. The device of claim 15, wherein the coupling mechanism comprises one or more of an adhesive, a suction cup, or a magnet between the body portion and a surface of the protective phone case.

17. The device of claim 15, wherein the coupling mechanism comprises one or more arms extending from the body portion and configured to releasably grip one or more edges of one of the smartphone or the protective phone case coupled to the smartphone.

18. The device of claim 15, wherein the one or more spacers are configured to maintain an air gap between the body portion and the protective phone case to dissipate heat.

* * * * *